(12) United States Patent
Joe

(10) Patent No.: US 9,101,611 B1
(45) Date of Patent: Aug. 11, 2015

(54) USE OF SULFONYLUREA (GLIMEPIRIDE) TO LOWER BLOOD GLUCOSE

(71) Applicant: Howard T Joe, Baytown, TX (US)

(72) Inventor: Howard T Joe, Baytown, TX (US)

( * ) Notice: Subject to any disclaimer, the term of this patent is extended or adjusted under 35 U.S.C. 154(b) by 0 days.

(21) Appl. No.: 14/269,371

(22) Filed: May 5, 2014

(51) Int. Cl.
*A61K 31/40* (2006.01)
*A61K 31/4015* (2006.01)

(52) U.S. Cl.
CPC .................................. *A61K 31/4015* (2013.01)

(58) Field of Classification Search
USPC .................................................. 514/408, 423
See application file for complete search history.

(56) References Cited

PUBLICATIONS

Nichols et al., Endocrine Practice, 2007, 13(1): 37-44.*

* cited by examiner

*Primary Examiner* — Rei-Tsang Shiao

(57) ABSTRACT

As it is generally known, when a medication fails to work properly it is increased in dosage and/or changed to another medication. Sulfonylurea medication has known to have secondary failure which increases blood glucose since the mid-1950s. (1)

From new research, I have found a new way to overcome sulfonylurea Glimepiride's effectiveness to continue lowering blood glucose when secondary failure occurs which increases blood glucose. The new way is made by stopping taking it for 3 or 5 days which automatically also lower blood glucose and then resuming it which further lowers more blood glucose like the first day taking it. It is assumed that it works because it fools the human body like it's the first day when resuming taking it.

1 Claim, No Drawings

USE OF SULFONYLUREA (GLIMEPIRIDE) TO LOWER BLOOD GLUCOSE

As the name implies, primary failure occurs when treatment drug fails when it is first given. Secondary failure happens when the treatment drug's effectiveness decreases with longer usage. Sulfonylurea drug like Glimepiride loses its ability to lower blood glucose by increasing blood glucose with longer period of usage. It was reported that sulfonylurea since the mid-1950s has secondary failure rate of about 21% in the first year of treatment and up to 46% within 2 years (1). Generally, when secondary failure occurs, it is time to increase medication and/or to change to another medication.

From new research, I found a new usage of sulfonylurea drug Glimepiride when secondary failure occurs. By stopping taking the Glimepiride tablets for 3 days which automatically also lower blood glucose and then resuming taking it recovers Glimepiride's effectiveness to lower blood glucose like the first day taking it. It is noted that the recovery effectiveness was first detected from stopping taking it for 5 days and then resuming taking it. It is likely that recovery works because stopping taking the drug fools the human body to assume like the first day taking it which it is claimed.

Since pre-diabetes and/or diabetes have used sulfonylurea drugs since the mid-1950s (1), there is no new matter or invention of sulfonylurea drugs in this patent application. The newness in this patent application is the usage of sulfonylurea drug like Glimepiride that fails to work when secondary failure occurs by stopping taking the tablet for 3 or 5 days which automatically also lower blood glucose and then resuming taking it that works like the first day taking it. In essence, it prevents the patient from taking more dosage of medication and/or changing to another different medication.

Since pre-diabetes and/or diabetes have used sulfonylurea drugs since the mid-1950s (1), there is no new matter or invention of sulfonylurea reported in this patent application. Moreover, the substitute specification contains no new matter. The newness in this patent application is the usage of sulfonylurea drug like Glimepiride that fails to work when secondary failure occurs by stopping taking the tablet for 3 or 5 days which automatically also lower blood glucose and then resuming taking it that works like the first day taking it. In essence, it prevents the patient from taking more dosage of medication and/or changing to another different medication.

The invention claimed is:

1. A method of treating diabetes or pre-diabetes in a patient comprising, when Glimepiride's secondary failure occurs for pre-diabetes/diabetes in a patient taking Glimepiride, and the blood glucose in said patient goes up high, then said patient stops taking Glimepiride for three or five days, then the blood glucose in said patient goes down low, then said patient resumes to take Glimepiride again, and Glimepiride works again to lower blood glucose in said patient.

* * * * *